(12) United States Patent
Sadano et al.

(10) Patent No.: US 7,214,379 B2
(45) Date of Patent: May 8, 2007

(54) METHOD FOR THE PURIFICATION OF MARIGOLD OLEORESIN

(75) Inventors: Shin Sadano, Kameoka (JP); Kazuhiro Fujiwara, Kameoka (JP); Koichi Harada, Kameoka (JP)

(73) Assignee: Riken Vitamin Co., Ltd., Tokyo (JP)

( * ) Notice: Subject to any disclaimer, the term of this patent is extended or adjusted under 35 U.S.C. 154(b) by 344 days.

(21) Appl. No.: 10/665,147

(22) Filed: Sep. 22, 2003

(65) Prior Publication Data

US 2004/0055954 A1    Mar. 25, 2004

(30) Foreign Application Priority Data

Sep. 20, 2002  (JP) .................... 2002-276105

(51) Int. Cl.
*C11B 1/10* (2006.01)
*A61K 36/28* (2006.01)
*B01D 11/00* (2006.01)

(52) U.S. Cl. ............... 424/195.18; 210/634; 424/764; 424/778; 514/912; 554/21; 554/206; 554/208

(58) Field of Classification Search .......... 210/634, 210/639; 554/9–14, 8, 20, 21, 206, 208; 424/451, 725, 778, 764, 195.18; 514/912, 514/962; 428/321.5, 402
See application file for complete search history.

(56) References Cited

U.S. PATENT DOCUMENTS

| | | | | |
|---|---|---|---|---|
| 4,048,203 | A | * | 9/1977 | Philip ..................... 554/208 |
| 5,288,550 | A | * | 2/1994 | Sakato ................. 428/321.5 |
| 5,308,759 | A | * | 5/1994 | Gierhart ................... 435/67 |
| 5,854,015 | A | * | 12/1998 | Garnett et al. ............ 435/67 |
| 5,932,101 | A | * | 8/1999 | Kanel et al. ............ 210/634 |
| 6,261,598 | B1 | * | 7/2001 | Runge et al. ........... 424/456 |
| 6,380,442 | B1 | * | 4/2002 | Madhavi et al. ........ 568/816 |
| 6,689,400 | B2 | * | 2/2004 | Majeed .................. 424/778 |
| 6,737,535 | B2 | * | 5/2004 | Kumar .................... 554/21 |
| 7,112,689 | B2 | * | 9/2006 | Sadano et al. .......... 554/206 |
| 7,150,890 | B2 | * | 12/2006 | Rosales et al. ......... 424/778 |
| 2003/0130531 | A1 | | 7/2003 | Sadano et al. ............ 554/9 |
| 2004/0267033 | A1 | * | 12/2004 | Rao et al. ................. 554/8 |

FOREIGN PATENT DOCUMENTS

| | | |
|---|---|---|
| EP | 1 325 943 | 7/2003 |
| JP | 61-268762 | 11/1986 |
| JP | 63-112659 | 5/1988 |
| JP | 2-38464 | 2/1990 |
| JP | 7-8202 | 1/1995 |
| JP | 7-8209 | 1/1995 |
| JP | 7-88303 | 4/1995 |
| JP | 8-168356 | 7/1996 |
| JP | 2003-201497 | 7/2003 |
| WO | 99/54408 | 10/1999 |
| WO | 02/060864 | 8/2002 |
| WO | 03/037833 | 5/2003 |

OTHER PUBLICATIONS

The Japan Health Industry News, Co., Ltd. Food Processing & Ingredients, No. 35, vol. 4, pp. 70-71, 2000, as well as its English Abstract.
Metamor Publishing Co., Ltd., Hoyoku Nishino and Khachik Frederic, Naze Multicarotene Ga Gan Wo Yokusei Surunoka (Why Does Multicarotene Suppress Cancer?), pp. 79-83, 1998, as well as its English Abstract.
Food Chemicals News Paper Inc., Food Stye 21, No. 3, vol. 3, pp. 50-53, 1999, as well as its English Abstract.
FFI Journal Editorial Committee, Foods & Food Ingredients Journal of Japan, No. 191, pp. 75-76, Mar. 2001, as well as its English Abstract.
The Japan Health Industry News Co., Ltd., Food Processing & Ingredients, No. 30, vol. 2, pp. 16-18, 1995, as well as its English Abstract.
Database WPI, Section Ch, Week 200305 Derwent Publications Ltd., London, GB, Class D13, AN 2003-047427 XP002263080 & CN 1 364 831 A, Aug. 21, 2002 * abstract *.
Database WPI, Section Ch, Week 200235 Derwent Publications Ltd., London, GB; Class D23, AN 2002-311245 XP002263081 & JP 2002 030068 A, Jan. 29, 2002 * abstract *.

\* cited by examiner

*Primary Examiner*—Joseph Drodge
(74) *Attorney, Agent, or Firm*—Wenderoth, Lind & Ponack, L.L.P.

(57) ABSTRACT

Marigold oleoresin having a low viscosity and a high lutein content which can be filled in soft capsules can be obtained according to the method of the present invention, which is characterized by combining a step of subjecting oleoresin to supercritical fluid extraction and a step of dissolving oleoresin in a ketone solvent, cooling the solution and removing the ingredient which precipitated in solution.

7 Claims, No Drawings

METHOD FOR THE PURIFICATION OF MARIGOLD OLEORESIN

BACKGROUND OF THE INVENTION

1. Field of the Invention

The present invention relates to a method for the purification of marigold oleoresin and a purified marigold oleoresin obtained according to the method.

2. Description of the Prior Art

The recent scientific researchers have reported that lutein, a kind of carotenoid, is associated with risk reduction for age-related macular degeneration (AMD) caused by oxidative damage to macular area of retina (for instance, cf. non-patent literature 1), and that lutein is effective for prevention of arteriosclerosis, prevention of cataract or suppression of carcinogenesis and etc. (for instance, cf. non-patent literatures 2, 3 and 4). Thus, lutein is useful as a health food, a dietary supplement, a food color, a pharmaceutical color and a medicinal drug.

Lutein is contained in fruits such as oranges, peaches, papayas, prunes and mangos in the form of lutein-fatty acid ester and is also present in many flowers and vegetables, particularly in petals of marigold flowers remarkably. Marigold oleoresin is obtained in the manner that dried and ground marigold flowers are extracted with a hydrocarbon solvent such as hexane, petroleum ether and etc. or with a chlorinated hydrocarbon solvent such as dichloromethane and etc., then the solvent is removed from the extract. Most of the commercially available marigold oleoresin is in form of a solid or a paste having a high viscosity at room temperature, and the content of lutein-fatty acid ester in oleoresin is usually 14 to 20% as ester (for instance, cf. patent literature 1).

In order to use lutein as a health food and a dietary supplement, soft capsules which encapsulate the said marigold oleoresin with gelatin film are prepared. Particularly when the content is oily, it is said that soft capsules are the best of all in terms of easy handling due to the encapsulation of a liquid, protection and stabilization of the contents, homogeneity of the contents, masking of taste and odor, and their highly value-added impression (cf. non-patent literature 5, etc.). Soft capsules are usually produced by die-cutting method in which a fixed amount of contents infused between 2 sheets of gelatin is punched out. To produce soft capsules of the said marigold oleoresin, it is necessary to liquidize the said marigold oleoresin by heating and fusing, because the content must be a liquid having a viscosity capable of being injected by a metering pump, not more than 20,000 cps, for instance, according to a rotary die method (cf. non-patent literature 5, etc.).

However, there is no warming and heating process at a temperature of not less than 40° C. in the production of soft capsules, since gelatin, a raw material of soft capsule, loses its formability at a temperature of not less than 40° C. (cf. non-patent literature 5, etc.). Thus, it is difficult to heat, fuse, and fill in the said marigold oleoresin.

For this reason a method of liquidizing the said marigold oleoresin at room temperature by diluting and dissolving with the addition of an edible vegetable oil is taken. This method, however, has a disadvantage that the number of capsules taken per one time or one day increases because of the decrease in a lutein content per one capsule.

In addition to the above, a product forming a slurry at room temperature and containing not less than 15% of total carotenoids which is produced by suspending lutein-fatty acid ester extracted from marigold flowers with an edible vegetable oil is commercially available. However, this product has a disadvantage, in addition to the low content of lutein-fatty acid ester, that it entirely becomes solid and is impossible to be filled in soft capsules when it is heated and fused at about 80° C. for sterilization and then cooled to room temperature.

(Patent literature 1)

International Publication No.99/54408 pamphlet (p. 2, line 24)

(Non-patent literature 1)

The Japan Health Industry News, Co., Ltd. FOOD PROCESSING & INGREDIENTS, No.35, vol.4, p. 70 (2000)

(Non-patent literature 2)

Metamor Publishing Co., Ltd., Hoyoku Nishino and Khachik Frederic, NAZE MULTICAROTENE GA GAN WO YOKUSEI SURUNOKA (Why does multicarotene suppress cancer?), p. 80 (1998)

(Non-patent literature 3)

Food Chemicals News Paper Inc., FOOD STYLE 21, No.3, vol.3, p. 52 (1999)

(Non-patent literature 4)

FFI Journal Editorial Committee, FOODS & FOOD INGREDIENTS JOURNAL OF JAPAN, No.191, p. 75–76 (March, 2001)

(Non-patent literature 5)

The Japan Health Industry News Co., Ltd., FOOD PROCESSING & INGREDIENTS, No.30, vol.2, p. 16 to 18 (1995)

SUMMARY OF THE INVENTION

An object of the present invention is to provide a method for obtaining marigold oleoresin which can be filled in soft capsules and has a high lutein content.

The present inventors have found, as a result of diligent studies to solve the above-mentioned problems, that marigold oleoresin having a low viscosity and a high lutein content is obtained by combining a step of subjecting oleoresin to supercritical fluid extraction and a step of dissolving oleoresin in a ketone solvent, cooling the solution and removing the ingredient which precipitated in solution such as phospholipids, etc. The present inventors have accomplished the present invention after further studies based on the findings.

Thus, the present invention is directed to the following (1) to (14).

(1) A method for producing marigold oleoresin which is characterized by carrying out a step of subjecting marigold oleoresin to supercritical fluid extraction and a step of dissolving marigold oleoresin in a ketone solvent, cooling the solution and removing the ingredient which precipitated in solution.

(2) A method for producing marigold oleoresin described in the above (1), which is characterized by carrying out a step of subjecting marigold oleoresin to supercritical fluid extraction and a step of dissolving marigold oleoresin in a ketone solvent, cooling the solution and removing the ingredient which precipitated in solution and isolating a purified marigold oleoresin of low viscosity and a high lutein content.

(3) A method for producing marigold oleoresin described in any one of the above (1) to (2), which is characterized by carrying out the step of supercritical fluid extraction in the presence of a diluent.

(4) A method for producing marigold oleoresin described in any one of the above (1) to (3), which is characterized by using a supercritical fluid selected from the group consisting of carbon dioxide, ethane, ethylene, propane, toluene and dinitrogen oxide.

(5) A method for producing marigold oleoresin described in any of the above (1) to (4), which is characterized in that the ketone solvent is acetone, methylethylketone or diethylketone.

(6) A method for producing marigold oleoresin described in any one of the above (1) to (5), wherein the step of supercritical fluid extraction is carried out using a carbon dioxide supercritical fluid under the condition that the carbon dioxide pressure is $(980$ to $2940) \times 10^4$ Pa $(=N/m^2)$ and the temperature is at critical temperature to 80° C.

(7) A method for producing marigold oleoresin described in any one of the above (1) to (5), wherein the step of supereritical fluid extraction is carried out using a carbon dioxide supercritical fluid under the condition that the carbon dioxide pressure is $(1470$ to $2450) \times 10^4$ Pa$(=N/m^2)$ and the temperature is at 40 to 60° C.

(8) Purified marigold oleoresin obtained by a method described in any one of the above (1) to (7).

(9) Purified marigold oleoresin described in above (8) having low viscosity and a high lutein content.

(10) Purified marigold oleoresin which contains not less than 20% of lutein-fatty acid ester and has a viscosity of not more than 20,000 mPa·s at 30° C.

(11) Purified marigold oleoresin described in the above (10) which contains not less than 30% of lutein-fatty acid ester and has a viscosity of not more than 20,000 mPa·s at 30° C.

(12) Purified marigold oleoresin described in the above (11), which has a viscosity of not more than 10,000 mPa·s at 30° C.

(13) Purified marigold oleoresin described in the above (12), which has a viscosity of not more than 5,000 mPa·s at 30° C.

(14) A soft capsule which contains the purified marigold oleoresin described in any one of the above (8) to (13).

The method for producing marigold oleoresin as described above is also a method for the purification of marigold oleoresin.

DETAILED DESCRIPTION OF THE INVENTION

Marigold oleoresin used in the present invention is obtained by drying flowers of marigold which is a member of the Compositae family (Tagetes erecta WILLD.), grinding the dried product, optionally converting into pellets, extracting with an organic solvent, usually hexane, and removing the solvent from the extract. The product is a solid or a paste at room temperature and has a specific odor. It contains lutein-fatty acid ester as the main component, usually together with fatty acid esters of zeaxanthin and cryptoxanthin. Therefore, the term lutein-fatty acid ester as used in the present invention should be construed as the general term encompassing all carotenoid esters including the carotenoid esters mentioned above.

In the method of the present invention, marigold oleoresin is subjected to supereritical fluid extraction using high-pressure carbon dioxide. Carbon dioxide is in a supereritical state at above the critical point (Temperature: 31.3° C., Pressure: 72.9 atm) and manifests a good solubility. Furthermore, a selective extraction can be carried out with such supereritical fluid by adjusting the pressure of a supereritical fluid supplied to an extraction vessel since the dissolving power of the supercritical fluid can be adjusted by changing pressure or temperature. The extraction vessel used for a step of supereritical extraction in the present invention may be the one which is well known per se in the present field. For instance, an extraction vessel shown in FIG. 2 in page 6 of the official gazette of Japanese Patent Publication S63-112659 can be used.

To be more precise, marigold oleoresin is placed in an extraction vessel as it is or with an edible oil and fat. As for the edible oil and fat used herein, a vegetable oil and fat such as rape-seed oil, corn oil, soybean oil, cotton-seed oil, sunflower oil, safflower oil, palm oil, coconut palm oil, etc.; an animal oil and fat such as a fish oil, etc.; or middle chain saturated fatty acid triglyceride, etc., are listed as examples. Addition of an edible oil and fat makes the viscosity of an extracted substance low and suppresses foaming, as a result the extraction procedure becomes easy. As for a diluent to adjust the viscosity of an extracted substance, other than the above-mentioned edible oils and fats, for instance, ethanol, hexane, acetone, glycerin, propylene glycol, etc. are used. The additional amount of these diluents may be about 10 to 100 parts by weight, preferably about 15 to 50 parts by weight, based on 100 parts by weight of marigold oleoresin.

Ethane, ethylene, propane, toluene, dinitrogen monoxide, etc. can be used as a supercritical fluid supplied to an extraction vessel, although carbon dioxide is popular. The components extracted by carbon dioxide in the supercritical state are recovered by evaporating carbon dioxide while decreasing the pressure in a separator vessel and is removed.

In the processing method of supercritical extraction, though it is not necessarily limited, separation of carbon dioxide from a solvent is carried out preferably on the condition of $(490$ to $588) \times 10^4$ Pa$(=N/m^2)$ and at the temperature of 40 to 60° C. after carrying out supercritical extraction under the critical condition of $(980$ to $2940) \times 10^4$ Pa$(=N/m^2)$, preferably $(1470$ to $2450) \times 10^4$ Pa$(=N/m^2)$ at critical temperature to 80° C., preferably at 40° C. to 60° C. Extracted components include a residual organic solvent, free fatty acids and a residue comprising accompanying substances which can be identified only to a certain extent, other than odor components. The edible oil and fat added as a diluent is almost completely extracted and removed on the condition of $1176 \times 10^4$ Pa$(=N/m^2)$ at not less than 40° C. The extraction time is, for instance, about 1 to about 30 hours, preferably about 3 hours to about 20 hours, but it is not limited to the above.

The end point of extraction is determined by extraction ratio as a criterion as it is difficult to identify the components affecting the viscosity of marigold oleoresin. Although an extraction ratio is a ratio of an extract to a substance to be extracted and varies depending on the quality of the substance to be extracted, extraction is usually carried out under the condition of extraction ratio of not less than 10%, preferably not less than 15%, more preferably not less than 20%.

Then, marigold oleoresin subjected to supercritical fluid extraction is dissolved in a ketone solvent. Examples of a ketone solvent used here are acetone, methylethylketone, diethylketone, etc., and acetone is preferable. The amount of acetone is 0.5 to 10 parts by weight, preferably 2 to 3 parts by weight, based on 1 part by weight of oleoresin.

A mixture of oleoresin and acetone is stirred for about 0.5 to 1 hour at 40 to 55° C., preferably at 45 to 50° C. while keeping moderate refluxing. The mixture is slowly cooled to 10 to 30° C., preferably 15 to 25° C. over a period of usually 2 to 4 hours. The cooled mixture is filtered through filter paper or filter fabric with filter aid, if necessary, such as diatomite. Purified marigold oleoresin is obtained by concentrating the filtrate under reduced pressure and removing therefrom acetone. The residual solvent in purified marigold oleoresin is removed at a temperature not exceeding 50° C., under reduced pressure, preferably in an atmosphere of nitrogen gas.

The method according to the present invention consists of the combination of a step of subjecting oleoresin to supercritical fluid extraction and a step of dissolving oleoresin in a ketone solvent, cooling the solution and removing the ingredient which precipitated in solution. Although either step may be carried out first, preferably a step of subjecting oleoresin to supercritical fluid extraction is carried out first, followed by a step of dissolving the extract in a ketone solvent, cooling the solution and removing the ingredient which precipitated in solution.

The purified marigold oleoresin obtained in the present invention is a liquid or a paste having a low viscosity at room temperature, in which the content of lutein-fatty acid ester is not less than 20%, sometimes not less than 30%. The said purified marigold oleoresin having the viscosity of not more than 20,000 mPa·s, preferably not more than 10,000 mPa·s, more preferably not more than 5,000 mPa·s is easily obtained. As a result of this, it has become possible to produce soft capsules containing highly concentrated lutein-fatty acid ester.

Soft capsules of marigold oleoresin obtained according to the present invention can be produced by the method known per se, such as immersion method, stamping method, dripping method, etc. The shape of soft capsule is not particularly limited and any shape such as football shape, oblong shape, spherical shape, triangular shape, teardrop shape, diamond shape, etc. may be employed, and among which a football shape is usually preferred. The amount of purified marigold oleoresin of the present invention per soft capsule is about 50 to 5,000 mg, preferably about 250 to 300 mg. Purified marigold oleoresin in soft capsules is stable for a long period of time. Soft capsules of marigold oleoresin are useful as a health food, a dietary supplement, a food color, a pharmaceutical color and a medicinal drug.

WORKING EXAMPLES

The following examples specifically illustrate the present invention.

A Method of Measuring the Content of Lutein-Fatty Acid Ester

About 0.1 g of test sample was accurately measured and dissolved in hexane to make a 100 ml solution. It was diluted with hexane so that the resultant solution had absorbance ranging from 0.3 to 0.7, and then the maximum absorbance of the diluted solution around 445 nm was measured by a spectrophotometer. The content of lutein-fatty acid ester was calculated by the following formula.

Content(%)=((Absorbance÷Weight of Sample)×Dilution Ratio)÷1,394×100 Note: 1,394 is absorbance coefficient at 445 nm.

Viscosity Determination

According to "Method 2: Rotatory Viscosity Determination" in "28. Viscosity Determination Method" mentioned in the 7th edition of THE JAPAN'S SPECIFICATIONS AND STANDARDS FOR FOOD ADDITIVES, viscosity was determined. For determination, No.4 rotor was used and number of rotation was chosen depending on presumed viscosity. Furthermore, the determination time of 30 seconds was fixed.

Example 1

100 g of marigold oleoresin (lutein-fatty acid ester: 16.9 wt %) was placed in a 1-L extraction vessel and, after supplying supercritical carbon dioxide of $1764 \times 10^4$ Pa(=N/$m^2$) at 50° C. into the vessel, subjected to extraction. The resulting extract solution was separated in a separator vessel under a decreased pressure of $490 \times 10^4$ Pa(=N/$m^2$) and a raised temperature of 60° C. As a result, 24.4 g of the extract was obtained.

Next, about 75 g of the extract residue was mixed with 190 ml of acetone and dissolved while heating the mixture to 50° C. The solution was slowly cooled to 20° C. over a period of about 3 hours, the generated insoluble substance was removed by filtration and the filtered solution was concentrated under reduced pressure. As a result, about 71 g of purified marigold oleoresin (lutein-fatty acid ester: 23.8 wt %) was obtained.

Example 2

100 g of marigold oleoresin (lutein-fatty acid ester: 23.3 wt %) and 30 g of rape-seed oil were placed in a 1-L extraction vessel and, after supplying supercritical carbon dioxide of $1764 \times 10^4$ Pa(=N/$m^2$) at 50° C. into the vessel, subjected to extraction. The resulting extract solution was separated in a separator vessel under a decreased pressure of $490 \times 10^4$ Pa(=N/$m^2$) and a raised temperature of 60° C. As a result, 50.1 g of the extract was obtained.

Next, 79.9 g of the extract residue was mixed with 210 ml of acetone and dissolved while heating the mixture to 50° C. The solution was slowly cooled to 20° C. over a period of about 3 hours, the generated insoluble substance was removed by filtration, and the filtered solution was concentrated under reduced pressure. As a result, about 76 g of purified marigold oleoresin (lutein-fatty acid ester: 30.5wt %) was obtained.

Example 3

100 g of marigold oleoresin (lutein-fatty acid ester: 26.9 wt %) was mixed with 250 ml of acetone and dissolved by warming to 50° C. The solution was slowly cooled to 20° C. over a period of about 3 hours and the generated insoluble substance was removed by filtration. The filtrated solution was concentrated under reduced pressure, as a result 94.8 g of the extract was obtained.

Next, 94.8 g of the extract and 30 g of rape-seed oil were placed in a 1-L extraction vessel and, after supplying supercritical carbon dioxide of $1764 \times 10^4$ Pa(=N/$m^2$) at 50° C. into the vessel, subjected to extraction. The resulting extract solution was separated in a separator vessel under a decreased pressure of $490 \times 10^4$ Pa(=N/$m^2$) and a raised temperature of 60° C., and 45.5 g of the extract was obtained. About 79 g of purified marigold oleoresin (lutein-fatty acid ester: 32.9 wt %) was obtained as the extract residue.

Viscosity of marigold oleoresin (starting material) and purified marigold oleoresin (product of the present invention) in Examples 1 to 3 is shown in Table 1.

TABLE 1

Viscosity of Marigold Oleoresin (30° C., Unit: mPa.s)

|  | EXAMPLE 1 | EXAMPLE 2 | EXAMPLE 3 |
|---|---|---|---|
| Starting material* | 24,000 | 31,000 | 40,000 |
| Product of the present invention** | 1,200 | 3,300 | 4,800 |

*Determination conditions: No.4 rotor, 6 rotation, 30 sec.
**Determination conditions: No.4 rotor, 60 rotation, 30 sec.

INDUSTRIAL APPLICABILITY

According to the present invention, marigold oleoresin having a low viscosity and a high lutein content is obtained by combining a step of subjecting oleoresin to supercritical fluid extraction and a step of dissolving marigold oleoresin in a ketone solvent, cooling the solution and removing the ingredient which precipitated in solution such as phospholipids, etc. The purified marigold oleoresin obtained according to the present invention can be filled in soft capsules and is useful as a health food, a dietary supplement, a food color, a pharmaceutical color and a medicinal drug.

What is claimed is:

1. A method for producing purified marigold oleoresin, which comprises:
    subjecting marigold oleoresin to supercritical fluid extraction, to obtain an extraction solution and an extraction residue;
    dissolving the extraction residue in a ketone solvent to obtain a solution;
    cooling the solution to form precipitates and removing the precipitates from the solution; and
    concentrating the solution, to thereby obtain the purified marigold oleoresin.

2. A method for producing purified marigold oleoresin, which comprises:
    dissolving marigold oleoresin in a ketone solvent to obtain a solution;
    cooling the solution to form precipitates and removing the precipitates from the solution;
    concentrating the solution;
    subjecting the concentrate to supercritical fluid extraction, to obtain an extraction solution and an extraction residue, to thereby obtain the purified marigold oleoresin as the extraction residue.

3. The method for producing purified marigold oleoresin claimed in claim 1 or 2, which is characterized by carrying out the step of supercritical fluid extraction in the presence of a diluent.

4. The method for producing purified marigold oleoresin claimed in claim 1 or 2, which is characterized by carrying out the supercritical fluid extraction using a supercritical fluid selected from the group consisting of carbon dioxide, ethane, ethylene, propane, toluene and dinitrogen monoxide.

5. The method for producing purified marigold oleoresin claimed in claim 1 or 2, which is characterized in that the ketone solvent is acetone, methylethylketone or diethylketone.

6. The method for producing purified marigold oleoresin claimed in claim 1 or 2, wherein the supercritical fluid extraction is carried out using a carbon dioxide supercritical fluid under the condition that the carbon dioxide pressure is (980 to 2940)×$10^4$ Pa (=N/$m^2$) and the temperature is at critical temperature to 80° C.

7. The method for producing purified marigold oleoresin claimed in claim 6, wherein the supercritical fluid extraction is carried out using a carbon dioxide supercritical fluid under the condition that the carbon dioxide pressure is (1470 to 2450) ×$10^4$ Pa(=N/$m^2$) and the temperature is at 40° C. to 60° C.

* * * * *